United States Patent [19]

Mount et al.

[11] Patent Number: 5,320,811
[45] Date of Patent: Jun. 14, 1994

[54] THIN LAYER CHROMATOGRAPHY DIRECT SAMPLE APPLICATION MANIFOLD

[75] Inventors: Dwight L. Mount, Duluth; Douglas W. Kirby, Flowery Branch; Duel L. Seymore, Jonesboro, all of Ga.

[73] Assignee: The United States of America as represented by the Department of Health and Human Services, Washington, D.C.

[21] Appl. No.: 729,960

[22] Filed: Jul. 15, 1991

[51] Int. Cl.$^5$ ............................................. B01L 11/00
[52] U.S. Cl. ...................................... 422/101; 422/70; 422/89; 422/104; 210/198.3
[58] Field of Search .................... 422/101, 70, 88, 89, 422/104; 436/161, 178; 210/198.2, 198.3, 656; 73/61.55, 61.54

[56] References Cited

U.S. PATENT DOCUMENTS

| | | | |
|---|---|---|---|
| 3,629,096 | 12/1971 | Hara | 210/198.3 |
| 3,667,917 | 6/1972 | Brandt | 73/61.54 |
| 3,757,952 | 9/1973 | Baitsholts et al. | 210/198.3 |
| 3,928,203 | 12/1975 | Kremer | 210/198.3 |
| 4,248,904 | 2/1981 | Fanimore | 210/658 |
| 4,272,381 | 6/1981 | Kremer et al. | 210/198.3 |
| 4,303,419 | 12/1981 | Frank et al. | 422/82 |
| 4,304,865 | 12/1981 | O'Brien et al. | 422/104 |
| 4,346,001 | 8/1982 | Tyihak et al. | 210/198.3 |
| 4,526,686 | 7/1985 | Sista et al. | 210/198.3 |
| 4,787,971 | 11/1988 | Donald | 422/70 |
| 4,810,471 | 3/1989 | Wachob et al. | 422/70 |
| 4,812,241 | 3/1989 | Shafer | 210/198.3 |
| 4,948,564 | 8/1990 | Root et al. | 422/101 |
| 4,966,695 | 10/1990 | Joshua | 422/104 |

FOREIGN PATENT DOCUMENTS 2131657 2/1972 Fed. Rep. of Germany ... 210/198.3

Primary Examiner—Robert J. Warden
Assistant Examiner—Hien Tran
Attorney, Agent, or Firm—Lowe, Price, LeBlanc & Becker

[57] ABSTRACT

An apparatus and method for directly applying a liquid sample matrix containing analytes and possible endogenous compounds to selected areas of a thin layer chromatographic sheet. The apparatus comprises a manifold made from an upper and lower filter block which are fastened together and supported on a support member. The thin layer chromatographic sheet is held between the upper and lower filter block. Samples are applied to the thin layer chromatographic sheet through aligned through-bores in the upper and lower filter block by connecting a syringe to the through-bores of the upper filter block. The method involves initially wetting areas of the thin layer chromatographic sheet where the sample is subsequently applied. Analytes retained on the thin layer chromatographic sheet are subsequently analyzed and may be further extracted from the thin layer chromatographic sheet for analysis.

9 Claims, 2 Drawing Sheets

THIN LAYER CHROMATOGRAPHY DIRECT SAMPLE APPLICATION MANIFOLD

TECHNICAL FIELD

The present invention relates to thin layer chromatography and more particularly, to an apparatus and method for applying a sample to a chromatographic sheet.

BACKGROUND ART

The chemical analysis of many compositions has been conducted successfully by spotting the compositions on a thin sheet of paper, glass or synthetic resin which carries an adsorbent coating on a surface thereof such as cellulose, silica gel, alumina, powdered nylon, powdered polyethylene, etc.

After the sheet has been spotted with one spot or a series of spaced spots of a test composition, it is dipped into a chromatographic eluant solvent such as benzene, alcohols, chloroform, water, etc. and developed in a closed chamber. During the development, the solvent migrates along the sheet, carrying components of the sample with it, with individual components of the sample travelling at different rates. The components are identified by comparison with a chromatograph of a known composition.

Usually the spots are applied by dissolving the test composition in a volatile solvent such as methyl alcohol, or acetone to form a liquid sample, and then repeatedly dabbing small quantities of the sample on the chromatographic sheet while allowing the solvent to evaporate between dabs. This is a slow, expensive procedure, and is also disadvantageous in as much as it is difficult to confine the sample to a well defined area.

Existing thin layer chromatographic technology requires that analytes be extracted from an aqueous matrix such as urine into an immiscible organic solvent after the pH of the matrix solvent has been adjusted to an appropriate value by the addition of another chemical or chemicals. This procedure requires; measured addition of the matrix solution, the organic solvent, and the pH adjusting solution into an extraction container; mixing of the contents of the extraction container; and usually centrifugation to break emulsions that form during this procedure. In some instances an aliquot of the organic phase may be applied directly to the chromatographic sheet for development and analysis. In many cases, for sensitivity reasons, the organic extract must be transferred to a clean container and the organic solvent removed by evaporation using a stream of some compressed gas, often at an elevated temperature using a water bath. The residue is reconstituted in a small volume of organic solvent for application.

The present invention provides substantial savings in labor and reduces the number of reagents and the equipment necessary to obtain a qualitative or quantitative result for a particular analytic in an aqueous matrix.

DISCLOSURE OF THE INVENTION

It is one object of the present invention to provide an apparatus for applying samples to a thin layer chromatographic sheet.

Another object of the present invention is to provide an apparatus for directly applying complex aqueous matrix samples to a thin layer chromatographic sheet.

A further object of the present invention is to provide a method of applying samples to a thin layer chromatographic sheet.

A still further object of the present invention is to provide a method of directly applying complex aqueous matrix samples to a thin layer chromatographic sheet.

According to these and further objects of the present invention which will become apparent as the description thereof is presented hereafter, there is provided by the present invention an apparatus for applying liquid samples to a chromatographic sheet comprising:

a manifold including:

an upper filter block having a plurality of stepped through-bores which define sample wells; and a lower filter block having a plurality of through-bores; and means for aligning and securing the upper filter block to the lower filter block with a chromatographic sheet positioned there between so that the stepped through-bores defining the sample wells in the upper filter block are aligned with the through-bores in the lower filter block.

Also provided for by the present invention is a method of applying liquid samples to a chromatographic sheet which involves:

securing a chromatographic sheet between an upper and lower filter block, the upper filter block having a plurality of stepped through-bores which define sample wells, and the lower filter block having a plurality of through-bores and a plurality of exit ports extending lengthwise from the through-bores;

wetting areas of chromatographic sheet which are aligned with the through-bores of the upper and lower filter blocks with a solvent;

passing a liquid sample matrix through the wetted areas of the chromatographic sheet; and retaining analytes from liquid the sample matrix on the chromatographic sheet in the wetted areas.

BRIEF DESCRIPTION OF DRAWINGS

The present invention will be described with reference to the attached drawings which are given by way of non-limiting examples only, in which.

BEST MODE FOR CARRYING OUT THE INVENTION

The present invention is directed to a manifold by which an aqueous medium such as urine, containing one or more analytes of interest may be forced through a small circular area of a flexible reverse-phase thin layer chromatographic (TLC) sheet using a disposable Luer-Lock syringe. As the aqueous medium passes through the TLC sheet, the analytes are absorbed onto the sheet along with various endogenous compounds which may be present in the aqueous medium, and are concentrated in the small circular area defined by the manifold.

The manifold is designed to allow application of a plurality of different aqueous medium samples and/or standard extracts onto corresponding circular areas approximately 1 cm from one end of a standard flexible TLC sheet, e.g., a 5×10 cm TLC sheet.

After application is complete, the TLC sheet is removed from the manifold and placed in a TLC development tank where the sheet is eluted by established techniques with a solvent system which separates the analytes from each other and from the endogenous compounds of the aqueous medium. After elution, the analytes are detected and quantitated with an appropriate detection scheme.

Figure 1:
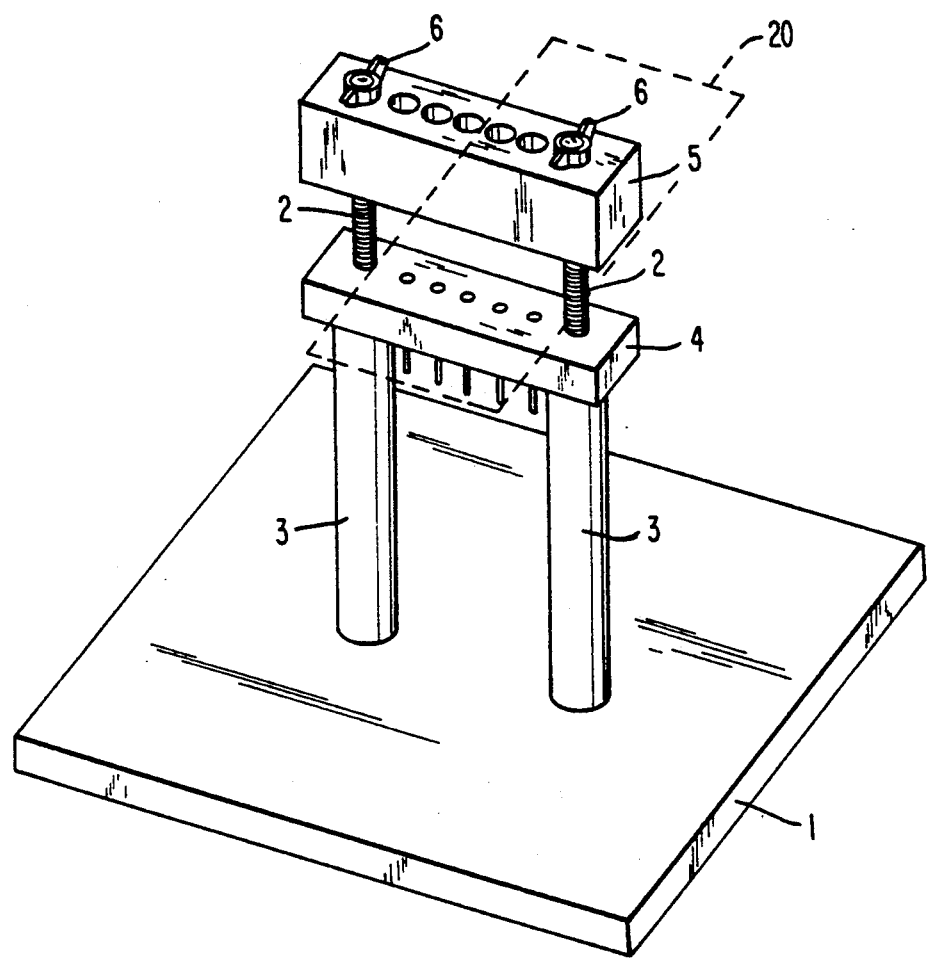
FIG. 1 is a perspective view of a sample application manifold according to a preferred embodiment the present invention.

The sample application manifold according to a preferred embodiment of the present invention is depicted in FIG. 1. As shown, the sample application manifold includes a base plate 1 to which a pair of threaded rods 2 are perpendicularly attached by suitable means such as complementary internally threaded bores in the base plate 1 or an equivalent fastening means. In further embodiments it is possible to permanently fix the threaded rods 2 to the base plate 1. Otherwise, the threaded rods 2 and the base plate 1 may be integrally formed.

A pair of spacers 3 are provided which serve as supports for the manifold assembly described below. The spacers 3 comprise sleeve elements having central axial through-bores through which the threaded rods 2 may pass when the spacers 3 are positioned as shown in FIG. 1. In an alternate embodiment the threaded rods 2 and spacers 3 may comprise an integrally formed support member, having a lower solid rod portion and an upper stepped down threaded portion.

The manifold assembly includes a lower filter block 4 and an upper filter block 5 which are supported by the spacers 3 and held in position by means of the threaded rods 2 and threaded fastening members 6, e.g. wing nuts, as shown in FIG. 1.

Figure 2:
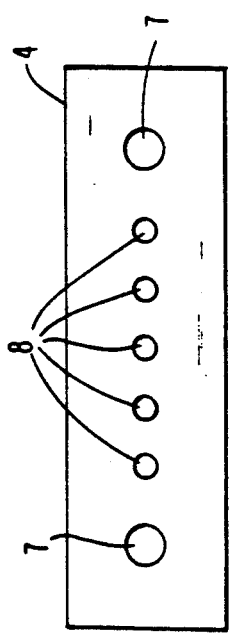
FIG. 2 is a top view of the upper filter block of the sample application manifold depicted in FIG. 1.
Figure 3:
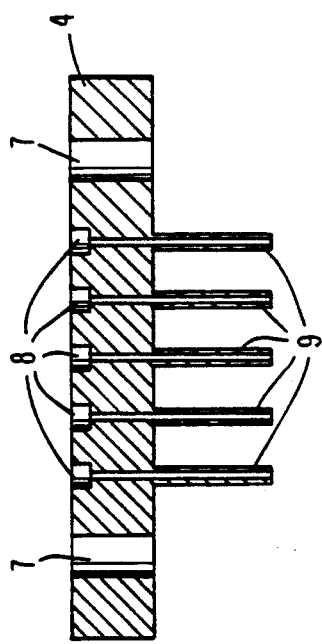
FIG. 3 is a side cross sectional view of the upper filter block of FIG. 2.
Figure 4:
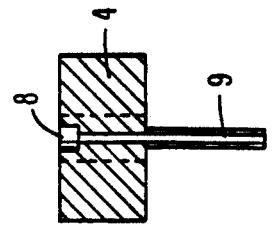
FIG. 4 is an end cross sectional view of the upper filter block of FIG. 2.

The lower filter block 4 is illustrated in FIGS. 2-4. The lower filter block 4 is made from a rectangular block of a suitably solid material such as metal, plastic, resinous material, etc., which is inert to or otherwise does not react or interfere with the aqueous medium or solvent system used in applying the aqueous medium to the TLC sheet. Although aluminum was used in initial experimentation without adverse effect when utilizing an aqueous matrix of urine, stainless steel was determined to be particularly preferable for purposes of the present invention.

As depicted in FIGS. 2-4, the lower filter block 4 includes a pair of through-bores 7 which are provided and arranged to receive the threaded rods 2 so that the lower filter block 4 may be positioned on and supported by the spacers 3 as shown in FIG. 1. Accordingly, the through-bores 7 have a diameter which is equal to or slightly larger than the diameter of the threaded rods 2. Moreover, the distance between the through-bores 7 is equal to the distance between the threaded rods 2.

A plurality of equally spaced through-bores 8 are provided along the center of the lower filter block 4 between through-bores 7. At the upper surface of the lower filter block 4 each of the plurality of through-bores 8 is counterbored as illustrated so as to have a slightly larger diameter at the upper surface of the lower filter block 4 so as to receive porous frits which support a flexible TLC sheet as discussed below.

Exit ports 9 are provided at the lower surface of the lower filter block 4. The exit ports 9 are tubular extensions of the through-bores 8 and serve the purpose of causing fluids to drip from the ends thereof rather than the lower surface of the lower filter block 4. As discussed below, this allows accurate determination of the amount of fluid passing through the manifold and a TLC sheet positioned therein.

Figure 5:
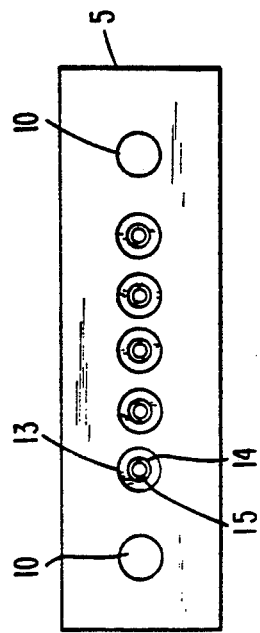
FIG. 5 is a top view of the lower filter block of the sample application manifold depicted in FIG. 1.
Figure 6:
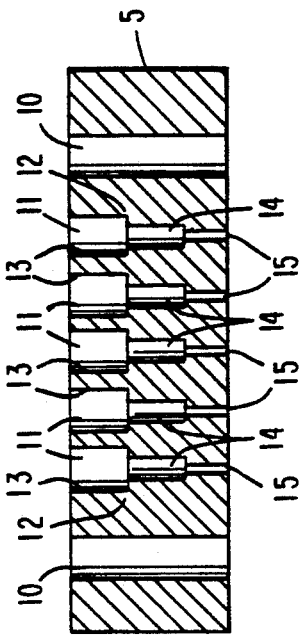
FIG. 6 is a side cross sectional view of the lower filter block of FIG. 5.
Figure 7:
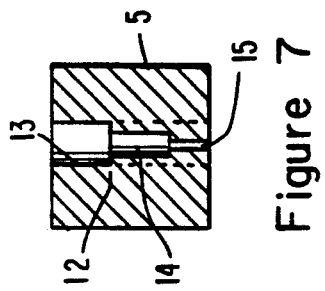
FIG. 7 is an end cross sectional view of the lower filter block of FIG. 5.

The upper filter block 5 is shown in FIGS. 5-7. The upper filter block 5 is made from a rectangular block of a suitable solid material such as metal, plastic, resinous material, etc., which is inert to or otherwise does not react or interfere with the aqueous medium or solvent system used in applying the aqueous medium to the TLC sheet. Although aluminum was used in initial experimentation without adverse effect when utilizing an aqueous matrix of urine, stainless steel was determined to be particularly preferable for purposes of the present invention.

As in the case of the lower filter block 4, the upper filter block 5 includes a pair of through-bores 10 which are provided to receive the threaded rods 2 so that the upper filter block 5 may be positioned on the threaded rods 2 and supported on the lower filter block 4 as shown in FIG. 1. Accordingly, the through-bores 10 have a diameter which is equal to or slightly larger than the diameter of the threaded rods 2. Moreover, the distance between the through-bores 10 is equal to the distance between the threaded rods 2.

As shown in FIGS. 6 and 7, the upper filter block includes a plurality of equally spaced stepped through-bores 11 provided along the center of the upper filter block 5 between through-bores 10. The stepped through-bores 11 define sample wells into which sample compositions are applied to be received onto a TLC sheet. The stepped through-bores 11 include an upper stepped portion 12 configured to have a shape which is substantially complementary to the dispensing end of a Luer-Lock syringe. In this regard, as shown in FIGS. 6 and 7, the upper stepped portion 12 of the through-bores 11 includes a first bore portion 13 and a second bore portion 14 which extends downwardly from the first bore portion 13 and has a diameter which is smaller than the first bore portion 13. Below the upper stepped portion, a lower through-bore portion 15 extends through the lower surface of the upper filter block 5.

In assembling the sample application manifold, the threaded rods 2 are fixed to the base plate 1 and the spacers 3 are positioned over the threaded rods 2 so that the spacers 3 rest on the base plate 1 and the free ends of the threaded rods 2 extend beyond the spacers 3. Optionally, washers may be provided over the threaded rods 2 so as to rest on the spacers 3. Next, the lower and upper filter blocks are positioned so that the through-bores 7 and 10 receive the threaded rods 2 and the lower filter block 4 rests on the upper end of the spacers 3 and upper filter block 5 rests on the lower filter block 4. After a TLC sheet 20 is positioned between the lower and upper filter blocks, fastening members 6, e.g., wing nuts, are utilized to tighten the lower and upper filter blocks together, as shown in FIG. 1.

EXAMPLE

In this example a sample application manifold was utilized in which the upper and lower filter blocks were 3.5 inches long and 1 inch wide. The lower filter block was 0.5 inches thick and the through-bores 8 where 0.081 inches in diameter. The counterbore at the upper surface of the lower filter block was 0.1 inches in diameter and 0.625 inches deep.

The upper filter block was 1.0 inch thick. The first bore portion of the upper stepped portion 13 of the through-bores 11 was 0.3124 inches in diameter and 0.375 inches deep. The second bore portion of the upper stepped portion 14 of the through-bores 11 was 0.100 inches in diameter and 0.750 inches deep. The lower through-bore portion 15 was 0.040 inches in diameter.

The through-bores 8 and lower through-bore portions 15 in the respective lower and upper filter blocks were equally spaced at 0.375 on center. The exit ports 9 of the lower filter block 4 were 0.75 inches long.

In this example the following procedure for determining the presence of the antimalarial drug, chloroquine, in urine was followed.

First, a 5×10 cm C18 (reverse-phase) Empore TLC sheet (Analytichem International, Harbor City, Calif.) was mounted in the sample application manifold. The TLC sheet was wetted by drawing 10% aqueous n-butylamine into a Luer-Lock disposable syringe and inserting or connecting the dispensing end of the syringe to the upper stepped portion of one of the through-bores 11 in the upper filter block.

After the Luer-Lock syringe was connected to the manifold, finger pressure was applied on the syringe plunger until 5 drops of solution dripped from the exit port of the manifold. The syringe was then removed and the urine sample was drawn into another Luer-Lock syringe and connected to the upper stepped portion of the through-bore where the n-butylamine had been previously applied. Finger pressure was applied on the syringe plunger until 10 drops of solution fall from the exit port of the manifold.

Solution wetting and sample application was continued in each of the plurality of through-bores 11 or sample wells, with the sample syringe being rinsed with water between samples.

After application of the samples was complete, the TLC sheet was removed from the manifold and rinsed with water. After rinsing, the TLC sheet was dried using a hot air gun, and placed in a TLC developing tank containing a solution of 90% methanol, 9.5% water, and 0.5% n-butylamine.

After the development was complete (about 1.5 hours) the TLC sheet was viewed under an ultraviolet lamp at 365 nm. A fluorescent spot with a bluish-purple color at the appropriate position on the TLC sheet indicated the presence of chloroquine.

In the above procedure, it was determined to be beneficial to provide a porous frit in the counterbored upper portions of the through-bore 8 in the lower filter block. For example, a 20 micron porous stainless steel frit $\frac{1}{8}$ inches in diameter and 0.063 inches thick was pressed in the counterbored upper portions of the through-bore 8 in the lower filter block. The surface of each frit was recessed below the surface of lower filter block by a distance of 0.050 inches. The presence of the frits allowed the flow of liquid through the manifold while providing support for the flexible TLC sheet so as to prevent rupture of the sheet which could have otherwise been caused by the pressure of the syringe-forced liquid against the sheet surface.

It was discovered during the course of the present invention that having the frit recessed below the upper surface of the lower filter block increased the rate and ease of the flow of the liquid through the TLC sheet as opposed to having the surface of the frit flush with the upper surface of the lower filter block. This increased rate and ease of flow is believed to be due to a slight stretching of the TLC sheet caused when the TLC is forced into the small (0.05 inch) cavity above the frit by pressure from the syringe-forced liquid.

In the above Example, it took about 15 seconds to apply the n-butylamine solution to each sample well. The n-butylamine was utilized to facilitate the adsorption of the chloroquine onto the TLC plate. It took 1-2 minutes to apply each urine sample, including the time for drawing each sample into the syringe and rinsing the syringe with water after sample application.

It was determined that the amount of sample which can be applied is dependent upon the amount of particulates and endogenous compounds in a particular sample. Clean, fresh samples worked best with the manifold system. Stored samples in which precipitates are observed should be filtered before application. For urine, a volume of 10 drops was determined to be the amount that could easily be applied utilizing the manifold of the above Example to achieve good sample reproducibility.

When applying urine samples to the manifold system in the above Example, it was noted that a small, insignificant amount of leakage of the urine between the upper manifold block and the TLC sheet sometimes occurred at the center sample well of the manifold. The leakage did not affect the results of the test since the volume of application was determined by counting drops that pass through the exit ports of the manifold. Only liquid which passes through the exit ports of the manifold has passed through the TLC sheet where adsorption of the sample occurs. The leakage was easily eliminated by providing the lower filter block with a raised ridge on the upper surface circumferening each of the sample wells.

Blank urine fortified to a concentration level of about 5 ppm with standard chloroquine was utilized as a comparison in the above Example. The chloroquine concentration of the fortified blank urine sample was determined by high performance liquid chromatographic analysis before and after passing the sample through the TLC manifold system. This experiment indicated that the system was better than 99% effective at removing chloroquine from the urine sample.

The present invention may be utilized to apply any type of sample to a TLC sheet as long as the sample matrix does not appreciably flow laterally through the TLC sheet. Such lateral flowing which may occur when attempting to adsorb polar analytes from an organic solvent on a bare silica TLC sheet which can result in unacceptable band spreading.

In addition to analysis of urine, other body fluids such as blood serum or plasma, and other aqueous sample matrices including organically polluted water are particularly suitable for analysis utilizing the present invention.

After sample application to a TLC sheet, the TLC sheet can be cut into sections along the length of the sheet so that each sheet section may be extracted with a particular solvent system in an extraction vessel. Each extract collected could then be subjected to established analytical methods such as gas chromatography to identify and quantify particular organic components, e.g., pollutants. In this manner, the method and apparatus of the present invention could provide a convenient means of extracting and concentrating organic components, e.g., pollutants, and a convenient pre-separation of the organic components before injection into a gas chromatographic system. This strategy could avoid the problem of co-elution of various components, a problem often encountered in the field of analytical analysis.

Although described above as being designed for use with 5×10 cm TLC sheets, the manifold could easily be designed to apply samples to 2.5×10 cm TLC sheets with a single sampling well or cavity 0.25 to 0.5 inches in diameter, or even with an oblong oval shaped well. Moreover, the manifold could easily be modified to support TLC sheets of any dimension.

Although the invention has been described with reference to particular means, materials and embodiments, from the foregoing description, one skilled in the art can easily ascertain the essential characteristics of the present invention and various changes and modifications may be made to adapt the various uses and conditions without departing from the spirit and scope of the present invention as described in the claims which follow.

What is claimed is:

1. A chromatography sample application device for applying liquid samples to a chromatographic sheet comprising:
    a manifold including:
        an upper filter block having a plurality of stepped through-bores which define sample wells; and
        a lower filter block having a plurality of through-bores; and
        means for aligning and securing said upper filter block to said lower filter block so that said stepped through-bores defining said sample wells in the upper filter block are in alignment with the through-bores in said lower filter block, said upper filter block and lower filter block providing opposed, planar surfaces which are complementary to planar surfaces of a chromatographic sheet for receiving and securing a chromatographic sheet therebetween such that liquid samples placed in said sample wells are applied to a chromatographic sheet positioned between said upper and lower filter blocks and flow through said plurality of through-bores.

2. A chromatography sample application device for applying liquid samples to a chromatographic sheet according to claim 1, wherein said lower filter block further includes exit ports aligned with said plurality of through-bores, said exit ports extending from a lower surface of said lower filter block.

3. A chromatography sample application device for applying liquid samples to a chromatographic sheet according to claim 2, further comprises a base plate and wherein said means for aligning and securing further comprises means to support said manifold above said base plate.

4. A chromatography sample application device for applying liquid samples to a chromatographic sheet according to claim 3, wherein said means to support comprises a pair of spaced apart threaded members which extend perpendicularly from the base plate which are receivable in corresponding pairs of through-bores in each of said upper and lower filter blocks.

5. A chromatography sample application device for applying liquid samples to a chromatographic sheet according to claim 4, wherein said means to support further comprises a pair of spacers which are positional over a portion said pair of threaded members.

6. A chromatography sample application device for applying liquid samples to a chromatographic sheet according to claim 1, wherein said stepped through bores of said upper filter block are complementarily shaped to a dispensing end of a syringe so that the syringe is connected to said sample wells by insertion into said stepped through-bores.

7. A chromatography sample application device for applying liquid samples to a chromatographic sheet according to claim 1, wherein said through-bores of said lower filter block include upper counterbored portions.

8. A chromatography sample application device for applying liquid samples to a chromatographic sheet according to claim 7, wherein said upper counterbored portions contain porous frits.

9. A chromatography sample application device for applying liquid samples to a chromatographic sheet according to claim 8, wherein said porous frits are recessed in said counterbored portions below an upper surface of the lower filter block.

* * * * *